United States Patent [19]

Messenger et al.

[11] Patent Number: 5,162,237
[45] Date of Patent: * Nov. 10, 1992

[54] REACTION CASSETTE FOR PREFORMING SEQUENTIAL ANALYTICAL ASSAYS BY NONCENTRIFUGAL AND NONCAPILLARY MANIPULATIONS

[75] Inventors: Lowry J. Messenger, Granger, Ind.; Christine D. Nelson, Edwardsburg, Mich.; Kin-Fai Yip, Elkhart; Frank W. Wogoman, Granger, both of Ind.

[73] Assignee: Miles Inc., Elkhart, Ind.

[*] Notice: The portion of the term of this patent subsequent to Feb. 5, 2008 has been disclaimed.

[21] Appl. No.: 774,362

[22] Filed: Oct. 8, 1991

Related U.S. Application Data

[63] Continuation of Ser. No. 378,039, Jul. 11, 1989, abandoned, which is a continuation-in-part of Ser. No. 179,843, Apr. 11, 1988, Pat. No. 4,990,075.

[51] Int. Cl.$^5$ .................. G01N 33/52; G01N 33/72
[52] U.S. Cl. .................. 436/523; 436/67; 436/165; 436/501; 436/533; 436/808; 436/536; 435/299; 435/312; 422/58; 422/61; 422/72; 422/102
[58] Field of Search .................. 422/55, 58, 61, 72, 422/102; 435/299, 312; 436/45, 17, 67, 165, 501, 518, 522, 523, 526, 528, 533, 536, 807, 808

[56] References Cited

U.S. PATENT DOCUMENTS

| | | | |
|---|---|---|---|
| 4,883,763 | 11/1989 | Holen | 436/45 |
| 4,970,171 | 11/1990 | Messenger et al. | 436/66 |
| 4,990,075 | 2/1991 | Wogoman | 422/58 |

Primary Examiner—James C. Housel
Assistant Examiner—David Redding
Attorney, Agent, or Firm—Andrew L. Klawitter

[57] ABSTRACT

Analytical reaction cassette and method for performing sequential analytical assay procedures to determine the amount of an analyte in a liquid test mixture. The reaction cassette can be in the form of a substantially square container having a substantially horizontal axis of rotation and incorporated with one or more analytical reagents such that they are contacted with a liquid test mixture in a desired ordered sequence to perform a particular assay procedure. Corners provided by the substantially square configuration of the reaction cassette disrupt the flow of liquids disposed in the reaction cassette upon contact therewith to thereby agitate and mix such liquids. A liquid disposed in the reaction cassette is capable of being manipulated and mixed therein by rotating the reaction cassette about the horizontal axis at sufficiently low velocities wherein the transport of such liquid is noncentrifugal and due substantially only to gravitational force. The reaction cassette is particularly useful for performing immunoturbidimetric assays, e.g., for the determination of glycated hemoglobin.

57 Claims, 6 Drawing Sheets

REACTION CASSETTE FOR PREFORMING SEQUENTIAL ANALYTICAL ASSAYS BY NONCENTRIFUGAL AND NONCAPILLARY MANIPULATIONS

CROSS-REFERENCE TO RELATED APPLICATION

This is a continuation of application Ser. No. 378,039, filed July 11, 1989, now abandoned, which is a continuation-in-part of application Ser. No. 179,843, filed Apr. 11, 1988, now U.S. Pat. No. 4,990,075.

BACKGROUND OF THE INVENTION

The present invention relates to analytical assay procedures for determining the amount of an analyte present in a test sample involving liquid analytical reactions between the analyte and one or more analytical reagents which require manipulative steps to make such determination. In particular, the present invention relates to a reaction vessel for performing sequential analytical reactions incorporated with one or more of such analytical reagents and which is capable of being manipulated by noncentrifugal forces to perform such analytical procedures by the noncapillary movement of fluids therein.

Various analytical procedures have been developed for the determination of analytes of industrial, environmental and particularly medical significance. In many instances, such analytical procedures require a number of analytical reactions which involve the manipulation of a liquid reaction mixture and which, in most instances, must be performed sequentially in order to carry out an assay protocol. Manipulations such as pipetting, mixing and agitation, periods of incubation, centrifugation, separation steps, and the like, are subject to errors that can lead to inaccurate results. Although various devices have been developed in an attempt to automate or otherwise simplify such manipulation, such devices are often cumbersome and require trained, experienced technicians for their operation. In some instances, such devices nevertheless still require a number of manual manipulative steps during the course of carrying out an assay protocol, particularly for performing sample transfer and mixing steps.

For example, U.S. Pat. Nos. 4,673,653 and 4,743,558 describe methods for performing biological analyses of liquid samples employing compartmentalized plastic containers which require a number of centrifugation steps. The containers comprise a storage chamber for a liquid sample, a calibration cell, a plurality of storage chambers for various reaction liquids, and a reaction vat. The various chambers, calibration cell and reaction vat are interconnected by capillary ducts for communicating liquids therebetween by centrifugal force. In carrying out the biological analyses, successive centrifugation steps are performed with the angular position of the containers being selected for each centrifugation step as a function of the orientation of a particular capillary duct relative to the direction of the centrifugal force in order to facilitate manipulation of a liquid disposed in the device.

Although various devices for performing analytical reactions have been proposed which do not require centrifugation steps, such devices nevertheless require a number of cumbersome manipulative steps which present the aforementioned problems. For example, U.S. Pat. No. 4,690,801 describes a manually manipulated device comprising a disk having a thin, flexible membrane applied to one side thereof which defines a conduit and a plurality of reagent reservoirs isolated from one another by frangible seals. An assay tube is situated at one end of the conduit and a sample injection reservoir is situated at the other end of the conduit. The disk fits into a base member, and a cover member having a roller bar fits over the base wherein the roller bar engages the surface of the disk. In operating the device, the cover is rotated relative to the disk wherein the roller bar applies pressure to the reservoirs to rupture the frangible seals and force the reagents from their respective reservoirs into the conduit for the purpose of carrying out the assay.

Similarly, other devices for performing analytical reactions which have been proposed in an attempt to overcome the problems presented by centrifugation and other cumbersome manipulative steps as described above are nevertheless complicated and, in some instances, expensive to manufacture. In addition, such devices do not provide simple and convenient steps for mixing analytical reagents with a test sample disposed in such devices.

For example, published German Patent Application No. 3706718 describes a device for carrying out heterogeneous reactions which comprises, as components thereof, a first capillary-active carrier incorporated with an insoluble reagent and located in a first measuring chamber, and a second capillary-active carrier incorporated with a soluble reagent in a first antechamber which is in capillary contact with the measuring chamber. A first introduction chamber, for receiving a sample and subsequent wash or elution solutions through a fill-opening in the device, is connected to the antechamber through a capillary structure, and the measuring chamber is further connected with an outlet chamber through a capillary structure through which a fluid is capable of flowing only under a given gravitational force. The capillary structure is essentially a one-dimensional grid which, due to the surface tension of a fluid arriving from above on the grid openings, initially does not permit the fluid to pass, and permits passage of fluid only under a predetermined pressure as determined by gravity.

Other embodiments of such capillary device are described as further including an additional introduction chamber and fill-opening, and a second antechamber connected over a third capillary with a mixing chamber which is connected to a fourth capillary with a measuring chamber. A spout protrudes into the mixing chamber over which fluid entering from the third capillary flows into the mixing chamber when the mixing chamber is tipped. A fifth capillary is also described which leads to the measuring chamber containing the first capillary carrier and connected with the first measuring chamber over a static one-way valve for capillary flow. The capillary carriers are characterized by their absorption capacity and their absorption strength which is defined according to the suction height to which they suction fluid in a given time.

However, such capillary device requires a number of internalized components for the assembly thereof which can often lead to expensive and complicated manufacturing procedures. In addition, the movement of fluid throughout the device relies upon the suctioning strength of carrier materials which could lead to inefficient and unreliable results if not properly selected.

Accordingly, it is an object of the present invention to provide a device for the necessary sample mixing and transfer steps for performing sequential analytical reactions in liquid test mixtures.

Another object of the present invention is to provide a device for performing sequential analytical assay procedures which does not rely upon centrifugal or capillary movement of liquids.

Still another object of the present invention is to provide a device for performing sequential analytical assay procedures which requires a minimal number of manipulation steps and which is easy to manipulate and operate.

Still further, another object of the present invention is to provide a device for performing sequential analytical assay procedures which is easily adaptable to a physician's office or a small clinical laboratory.

SUMMARY OF THE INVENTION

The present invention provides a self-contained reaction cassette or vessel and a method for performing analytical assay procedures involving sequential analytical reactions in a liquid test mixture between an analyte and one or more analytical reagents which react with the analyte to produce a detectable signal. The device is particularly useful for performing immunoassays which typically require a number of mixing steps, as well as other cumbersome manipulative steps, such as pipetting and incubation of a test sample and liquid test mixtures. The necessary sequential reagent addition and mixing steps are accomplished within the device by (a) the noncentrifugal rotation of the device at relatively low velocities resulting in the gravitational flow of a liquid mixture to zones or areas in the device designed for performing the various functional steps of the assay, and (b) oscillation of the device to agitate the liquid mixture in contact with flow disrupting means, such as a corner of a square-shaped cassette.

According to the invention, the device is incorporated with one or more of the necessary analytical reagents for carrying out a particular sequential analytical assay procedure. A liquid test mixture is formed in the device and can be sequentially contacted and reacted with the analytical reagents by the noncapillary manipulation thereof, and the resulting liquid mixtures agitated and mixed at relatively low velocities, without the need for additional external manipulative steps to complete the assay. The device also permits the convenient measurement of the detectable response produced by the analytical reactions between the analyte and the analytical reagents and, where one or more detectable responses are produced subsequent to or during the performance of the assay, the device can be easily manipulated to permit the convenient measurement thereof in the device during the course of the assay.

In particular, the device is a cassette or container having a substantially horizontal axis of rotation, preferably a substantially central axis of rotation, and comprising a reaction channel and inlet means in open liquid flow communication with the reaction channel for introducing a test sample into the reaction channel, preferably in the form of an inlet port. The reaction channel comprises at least one reagent zone incorporated with an analytical reagent, preferably as a dry form thereof, and means for disrupting the flow of a liquid mixture by gravity along the reaction channel sufficient upon agitation to thoroughly mix the liquid mixture in contact therewith. In a preferred embodiment, the device further comprises means for introducing a test sample into the reaction channel through the inlet means, preferably in the form of a capillary device which is capable of being inserted through and thereby closing the inlet means. In a further preferred embodiment, the device comprises liquid delivery means incorporated with a liquid reagent which is capable of being manipulated in order to introduce the liquid reagent into the reaction channel during the course of performing an analytical assay procedure. Preferably, the liquid delivery means is in the form of a reservoir body closed by an externally manipulable, removable, fluid tight seal.

The flow disrupting means can either be situated along the reaction channel a sufficient distance from the reagent zone that a liquid mixture can be present in the reagent zone without simultaneously being in contact with the flow disrupting means, or the flow disrupting means and the reagent zone can be situated sufficiently proximate to each other that a liquid mixture can be present in the reaction channel in contact with the flow disrupting means and the reagent zone simultaneously. Rapid oscillation of the device such that the liquid therein is in contact with the flow disrupting means results in a sufficient amount of turbulence in the liquid to thereby efficiently agitate and mix the liquid. Preferably, the flow disrupting means comprises perimeter and inner wall portions of the reaction channel which are configured such that the flow of a liquid are redirected upon contact of the liquid therewith. In a preferred embodiment, the wall portions are configured to provide one or more corners in the reaction channel which each form an angle of between about 75 degrees and about 105 degrees, more preferably about 90 degrees, which corners serve as suitable flow disrupting means. One or more of the corners can also serve as a viewing zone from which the detectable response can be detected and measured.

According to the invention, a liquid test mixture disposed in the reaction channel can be transported by gravity along the reaction channel between one or more reagent zones and the flow disrupting means by rotating the device relatively slowly about the horizontal axis. Accordingly, once a liquid test mixture has been formed in the device, an analytical assay procedure, including the agitation and mixing of the liquid test mixture with the analytical reagents, can be carried out by simply rotating and oscillating the device without the need for additional pipetting, centrifugation, or otherwise complicated manipulative steps to transfer the liquid test mixture from one analytical reagent to another or, for example, to a cuvette for detecting and measuring the detectable response.

An analytical assay procedure employing the device of the present invention in general terms is performed by introducing a test sample into the reaction channel through the inlet means. A liquid test mixture is formed and brought into contact with the analytical reagent incorporated in the reagent zone, preferably by rotating the device about the horizontal axis whereby the liquid test mixture is transported by gravity along the reaction channel to the reagent zone to form a further liquid mixture with the analytical reagent incorporated therein. In forming the liquid mixture or subsequent thereto, the device is oscillated about the horizontal axis such that the liquid mixture is agitated in contact with the flow disrupting means to thereby mix the liquid mixture as described above. The detectable response in the liquid mixture is thereafter measured.

According to a preferred embodiment of the present invention, the reaction channel comprises additional reagent zones incorporated with one or more additional analytical reagents situated in fluid flow contact along the reaction channel, and a liquid reagent is contained in a centrally located liquid delivery means as described above. An analytical assay procedure is carried out by introducing a test sample into the reaction channel and introducing the liquid reagent into the reaction channel. It is to be understood that depending upon the particular assay protocol, the liquid reagent can be introduced and mixed with the test sample either prior to contacting the liquid test sample with one or more of the analytical reagents in the reagent zones, or can be introduced subsequent thereto. In either case, the device is further rotated about the horizontal axis to thereby form additional liquid mixtures, and the additional liquid mixtures agitated and mixed by contacting flow disrupting means as described above.

As will be described in greater detail hereinafter, the device of the present invention is not intended to be limited to analytical assay procedures as described above, but can be employed to carry out substantially any sequential analytical assay procedure involving a number of manipulative steps in a desired ordered sequence and a plurality of analytical assay reagents. In addition, the open liquid flow communication provided along the reaction channel permits the measurement of one or more additional detectable response by rotating the device about the horizontal axis whereby a liquid test mixtures can be transported by gravity along the reaction channel to one or more viewing zones for multiple measurements during the course of a single assay.

DESCRIPTION OF THE PREFERRED EMBODIMENTS

Figure 1:
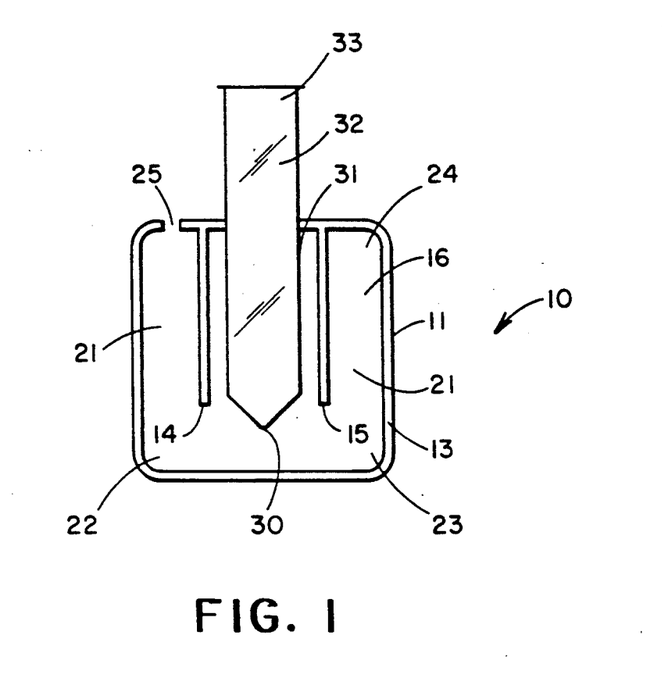
FIG. 1 is a front view of an illustrative device of the present invention.
Figure 2:
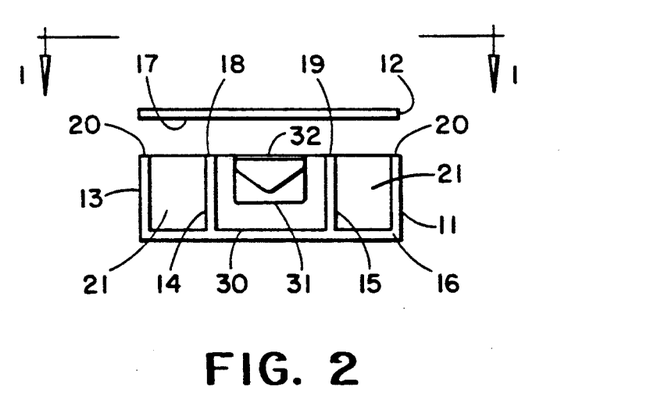
FIG. 2 is a bottom view of the device shown in FIG. 1.

Referring now to FIGS. 1 and 2, the device 10 (FIG. 1) of the present invention is preferably in the form of a substantially square cassette or container having a substantially horizontal axis of rotation and comprises an open body member 11 which is closed by a lid member 12 (FIG. 2). The external dimensions of the cassette are not critical, although normally the cassette will have a height and width roughly between 3 cm and 15 cm and a thickness of between 0.25 cm and 2 cm. A particularly suitable cassette would have a height and width of about 6 cm and a thickness of about 1 cm. Body member 11 and lid member 12 are preferably provided as separate components in order to permit the incorporation of one or more analytical reagents therein, as will be described in greater detail hereinafter, prior to assembly of the cassette. Once the analytical reagents have been incorporated into body member 11, body member 11 is closed by lid member 12 which is then glued, laser or sonic welded, or otherwise permanently fastened thereto according to methods known in the art to provide a fluid-tight seal.

Body member 11 comprises a perimeter side wall 13 and first and second inner walls 14 and 15, respectively, situated on and positioned substantially perpendicular to an outer support wall 16. Side wall 13 and first and second inner walls 14 and 15 are substantially equal in height so that when body member 11 is closed by lid member 12, the inner surface 17 of lid member 12 rests substantially against the upper edges 18 and 19 of first and second inner walls 14 and 15, against the upper edge 20 of side wall 13, and sealed thereto in a fluid-tight manner. Side wall 13, together with the contiguous portions of lid member 12 and outer support wall 16, forms a reaction channel 21 which extends around the perimeter of side wall 13 and forms first, second and third corners 22, 23, and 24 which, according to the present invention, provide means for disrupting the flow of a liquid mixture upon agitation in contact therewith, and, in addition, also serve as a viewing zone (or zones) for detecting and measuring the detectable response provided by a liquid reaction mixture. An inlet port 25 is situated in side wall 13 at the proximal end of reaction channel 21 for introducing a test sample into reaction channel 21, such as with a pipet or the like. Preferably, inlet port 25 is stoppered, plugged or otherwise closed subsequent to the introduction of a test sample into device 10 in order to prevent liquid loss when manipulating device 10 during and after the course of an assay.

According to the invention, one or more analytical reagents can be incorporated into reagent zones situated along reaction channel 21, preferably in a dry form, either in areas proximate to or generally between corners 22, 23 and 24. In either case, a liquid disposed in reaction channel 21 can be freely transported by gravity along reaction channel 21 and between corners 22, 23 and 24, by rotating device 10 about the horizontal axis. In addition to the incorporation of one or more analytical reagents in reagent zones along reaction channel 21, device 10 further includes a liquid delivery reservoir 30 adapted to contain a buffer and/or liquid reagent for performing an analytical assay procedure, preferably from between about 0.25 mL and about 10 mL, more preferably from between about 0.4 mL and about 1.0 mL. Liquid delivery reservoir 30 comprises a reservoir body 31 which is closed by a seal or membrane 32 in a fluid-tight manner. Membrane 32 can be selected from a variety of materials, preferably substantially manipulable and flexible materials which are capable of closing reservoir body 31 in a fluid-tight manner, such as with adhesives known in the art which are capable of providing a fluid-tight seal, and which can be readily removed whereby the liquid reagent freely flows downward out of reservoir body 31 and into reaction channel 21. As will be described in greater detail hereinafter, the distal end 33 of membrane 32 is, for example, pulled in a direction away from device 10 to remove or peel membrane 32 from reservoir body 31 and thereby introduce the liquid reagent contained in reservoir body 31 into reaction channel 21. It is to be understood, of course, that other devices known in the art can be incorporated into device 10 to serve as a liquid delivery system for introducing a liquid reagent as described above. For example, a syringe-like device (not shown) comprising a tubular body containing a liquid reagent and a reciprocating plunger member can instead be incorporated into device 10, and the plunger manipulated to express the liquid reagent into reaction channel 21 when desired.

The operation of device 10 according to the present invention as described herein depends upon the substantially free and noncapillary gravitational flow of a liquid along reaction channel 21. As will be understood by one skilled in the art, such free gravitational flow can be substantially hindered by surface tension, air pockets, and other physical phenomena which frequently occur when a liquid is in substantial contact with one or more solid surfaces or, for example, when disposed in a capillary duct, tube or the like. Accordingly, such free gravitational flow of a liquid in device 10 will depend upon the open, internal dimensions of reaction channel 21, as well as the relative volume of the liquid disposed therein. Such internal dimensions of device 10 will normally be of sufficient size to accommodate and, at the same time, vent the liquid as it is manipulated throughout the device 10. Although the dimensions of device 10 are preferably substantially of the size shown in the drawings and as described above, one skilled in the art apprised of the foregoing considerations can modify the dimensions of device 10 or otherwise provide for the free gravitational flow of a liquid therein. For example, the device 10 can include air vents or openings to permit the escape of air from device 10 as a liquid is manipulated therein and thereby prevent the formation of air pockets or prevent the occurrence of other physical phenomena which could otherwise hinder the free gravitational flow of a liquid. Such vents or openings will be situated at an area or areas of device 10 or otherwise constructed to prevent the escape of a liquid from device 10.

In order to provide for the free gravitational flow of a liquid or reaction mixtures thereof, it is preferred that the volume thereof be less than that volume which will substantially occupy or fill the area of liquid flow movement between upper and lower, or adjacent, walls such as, for example, the area between perimeter wall 13 and first and second inner walls 14 and 15. Preferably, the total volume of liquid present in reaction channel 21 can be from between about 0.25 mL and about 10 mL, more preferably from between about 0.4 mL and about 1.0 mL, in order to be freely transported by gravity in device 10 in accordance with the teachings of the present invention. In addition, the surfaces of device 10 can be treated according to methods known in the art to provide a wettable or hydrophilic surface in order to permit the free flow of a liquid therealong and to substantially prevent surface tension or other physical phenomena from occurring during the course of an assay procedure. Such treatment of the surfaces includes, but is not intended to be limited to, plasma treatments such as plasma etching and plasma polymerization, corona discharge, wet chemical treatment and coating technologies known in the art, and the like.

For purposes of moving the liquid mixture in the cassette from one position or station to another, e.g., from one reagent zone to another or from a reagent zone to a mixing or viewing zone, device 10 is normally rotated about the horizontal axis at a speed that is sufficiently slow such that the transport of a liquid along reaction channel 21 is essentially noncentrifugal and due substantially only to gravitational forces. Also, while rotation of the cassette can include rotations up to 360° or even multiple revolutions of the device, normally device 10 will be rotated over substantially short distances or increments and in a manner that the movement of a liquid or mixtures thereof disposed in the device is the result of the gravitational forces exerted upon the liquid. For purposes of illustration, the noncentrifugal rotations intended to move the liquid mixture from one location to another in the device will normally be over rotational arcs greater than about 25°, more usually greater than about 45°. Accordingly, the gravitational movement of a liquid or mixtures thereof in device 10 is accomplished by the noncentrifugal rotation of device 10, and is not intended to be accomplished by centrifugal forces which would be substantially greater than the gravitational force exerted upon a liquid. Preferably, in order to accomplish liquid movement operations, device 10 is generally rotated about the horizontal axis at a peak speed of between about 1 revolutions per minute (r.p.m.) and about 60 r.p.m., more preferably between about 15 r.p.m. and about 40 r.p.m. Such noncentrifugal, rotational speed will of course depend upon the size of device 10 and can be determined by one skilled in the art apprised of the foregoing considerations.

On the other hand, the oscillations employed to obtain mixing of the liquid mixture in contact with the flow disrupting means, e.g., corners 22, 23 or 24, generally will involve rotational speeds over a short distance in excess of 10 r.p.m. Preferably, the maximum speed of rotation achieved in mid-cycle of an oscillation for this purpose will be between about 15 r.p.m. and about 40 r.p.m. While such speeds, if exerted over significantly longer arcs of rotation, e.g., if exerted for full rotations, might result in significant centrifugal force being applied to the liquid mixture, as described above, such oscillations are maintained over a rather narrow range of movement such that any centrifugal forces only aid in the mixing action produced at the flow disrupting means.

It is to be understood that the configuration of reaction channel 21 is not intended to be limited as described above, and that additional corners or other configurations can be provided along reaction channel 21 to serve as flow disrupting means or to provide additional reagent zones or areas in accordance with the teachings of the present invention. Accordingly, a particularly preferred embodiment of the present invention and its use in performing a sequential analytical assay procedure will now be described in order to provide a better understanding of the present invention.

Figure 3:
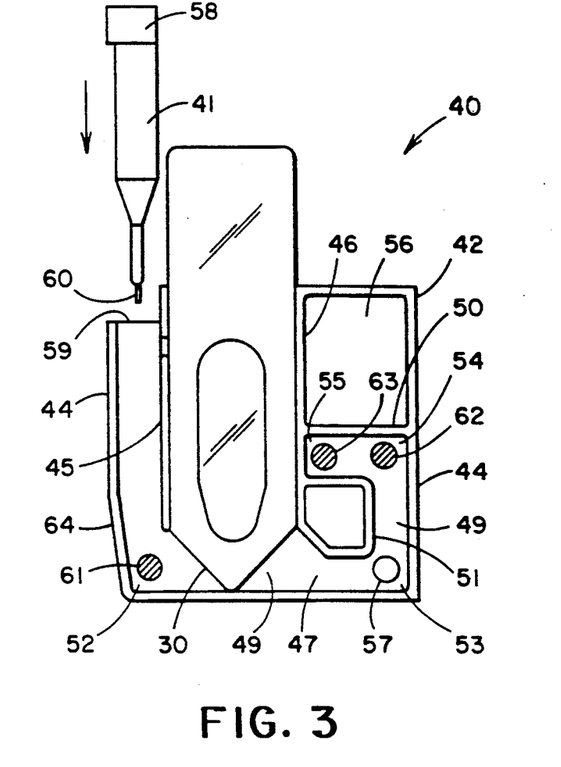
FIG. 3 is an exploded front view of a preferred embodiment of the present invention.
Figure 4:
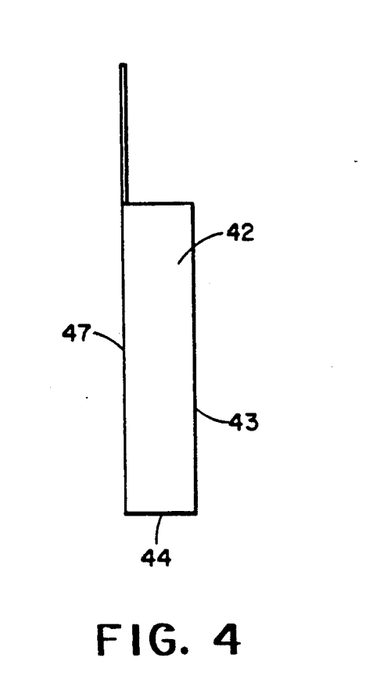
FIG. 4 is a side view of the device shown in FIG. 3.

Referring to FIGS. 3-5, there is shown a cassette 40 and a capillary holder 41 for introducing a predetermined amount of a liquid test sample into device 40. Typical dimensions of such device are the same as described above with respect to the device of FIGS. 1 and 2. Device 40 comprises a body member 42 which is closed by a lid member 43 in a fluid-tight manner as previously described. Body member 42 comprises a perimeter side wall 44 and first and second inner walls 45 and 46, respectively, situated on and substantially perpendicular to an outer support wall 47, and liquid delivery reservoir 30 as described above is situated between first and second inner walls 45 and 46. Side wall 44, together with the contiguous portions to lid member 43 and support wall 47, forms an analytical reaction channel 49, a portion of which is U-shaped and formed by a third inner wall 50 which extends between and substantially perpendicular to second inner wall 46 and side wall 44, and a fourth inner wall 51 which extends from second inner wall 46. First and second corners 52 and 53, respectively, are formed by side wall 44 along reaction channel 49. A third corner 54 is formed by side wall 44 and third inner wall 50, and a fourth corner 55 is formed by and between second, third and fourth inner walls 46, 50 and 51, respectively. It is to be understood that a closed area 56 of the device 40 is nonfunctional but, if desired, third inner wall 50 and fourth inner wall 51 could be removed, modified or otherwise reconfigured to further extend reaction channel 49 into the portion identified as closed area 56. Second corner 53 serves as a viewing zone for measuring detectable responses produced by the reaction of the various reagents with the test sample. Lid member 43 and side wall 44 are formed with a substantially transparent cuvette window 57 in corner 53 to permit the accurate measurement of detectable signals such as absorbance or turbidity.

Capillary holder 41 comprises a distal end 58 configured to matably engage with inlet port 59 in side wall 44 and a proximal end which includes a capillary sampling tube 60. The liquid capacity of capillary tube 60 will depend upon the particular analytical assay procedure which is to be performed in device 40, and, accordingly, will vary in size to introduce a predetermined amount of a liquid test sample into device 40. It is to be understood, of course, that other means for introducing a liquid test sample into device 40 can also be employed, such as with a pipet or the like, wherein inlet port 59 can be similarly closed with, for example, a plug member (not shown) or other means to prevent the loss of liquid during the course of an assay.

Reagent zones 61, 62 and 63 are situated at first, third and fourth corners 52, 54 and 55, respectively, and are incorporated with analytical reagents for performing a particular analytical assay procedure. The analytical reagents are preferably present in the reagent zones in a substantially dry, water soluble, suspendable, or dissolvable form, and can be incorporated along reaction channel 49 according to methods known in the art, such as by noncovalent binding technique, absorptive techniques, and the like, in the desired order in which they are to be sequentially contacted with a liquid test sample. Alternatively, a reagent pad comprising, for example, an absorbent material, such as a woven fabric, a bibulous material, and the like, or a reagent film, can be incorporated with an analytical reagent according to methods known in the art and attached to a surface of reaction channel 49 which is contacted with a liquid. It is to be understood, of course, that such analytical reagents can be incorporated on or at any surface along reaction channel 49 which will be contacted by a liquid disposed therein. For example, the reagent zones can be situated on a surface of side wall 44, outer wall 47, or an inner surface of lid member 43 at the desired location of a respective reagent zone along reaction channel 49. In some applications, it will be preferable to place reagent zone 63 on the inner surface of lid member 43 opposite the reagent zone 62 on side wall 44. Such disposition of reagent zones 62 and 63 enables essentially simultaneous contact of the incorporated reagents with a liquid mixture transported along reaction channel 49.

A particularly advantageous reagent zone will be in the form of a substantially flat, raised portion or mesa-shaped node on the surface of a selected area of device 40 along reaction channel 49. An analytical reagent can be incorporated in such a zone by applying a liquid form of the particular analytical reagent to the mesa and permitting the liquid portion thereof to evaporate to thereby deposit a dry form of the analytical reagent thereto. The volume of the liquid form of the analytical reagent will depend, of course, upon the surface area of the mesa, and will preferably be from between about 0.002 mL and about 0.1 mL, more preferably from between about 0.005 mL and about 0.015 mL. As will be understood by one skilled in the art, the surface tension of a liquid which is deposited onto such mesa will prevent the liquid from spreading to adjacent surfaces and thereby provides a discrete or localized area to serve as a reagent zone. The use of a mesa to incorporate an analytical reagent is particularly useful during the manufacturing processes since device 40 can be easily molded or otherwise manufactured with one or more mesa at predetermined locations which can serve as reagent zones, and, accordingly, permits easy and convenient incorporation of analytical reagents prior to assembly of device 40.

Referring now to FIGS. 5(a)–5(h), device 40 is shown in various rotational positions to further illustrate the gravitational flow and mixing of a liquid mixture along reaction channel 49, and the sequential contact thereof with corners 52, 53, 54 and 55, and analytical reagents incorporated into reagent zones 61, 62 and 63 along reaction channel 49 when the device 40 is rotated about the horizontal axis as described above. The solid arrows shown outside device 40 indicate the direction of rotation of device 40 about its horizontal axis, and the broken arrows shown within device 40 indicate the direction of liquid flow when device 40 is rotated about its horizontal axis in the direction of the solid arrows.

It is to be understood that FIGS. 5(a)–5(h) are for purposes of illustration only, and are not intended to limit the number, nature or manner of incorporation of analytical reagents into device 40, or the sequence or direction of rotation of device 40. For example, although three reagent zones 61, 62 and 63 are shown, other assay procedures can also be performed in device 40 with the number of analytical reagents will of course depending upon the particular assay requirements. Furthermore, the device can include less than the required number of analytical reagents for performing an analytical assay procedure where one or more reaction mixtures thereof can first be formed outside of the device and then introduced into the device to complete the assay.

Figure 5A:
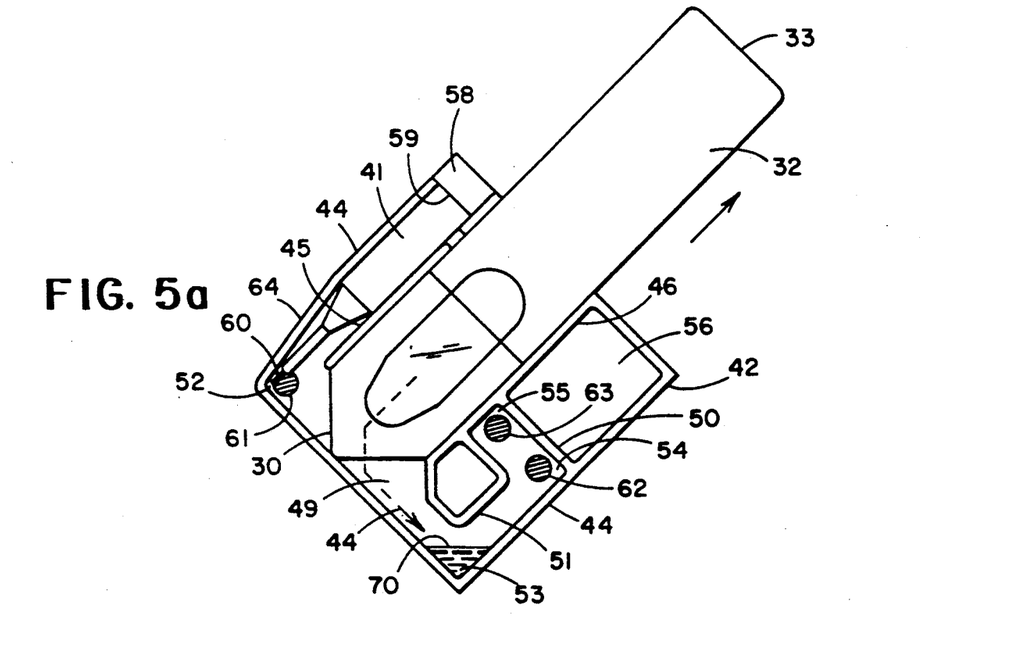
FIGS. 5a-5h are a sequence of front views of the preferred device of FIGS. 3 and 4 illustrating the performance of an analytical test method using such device.
Figure 5B:
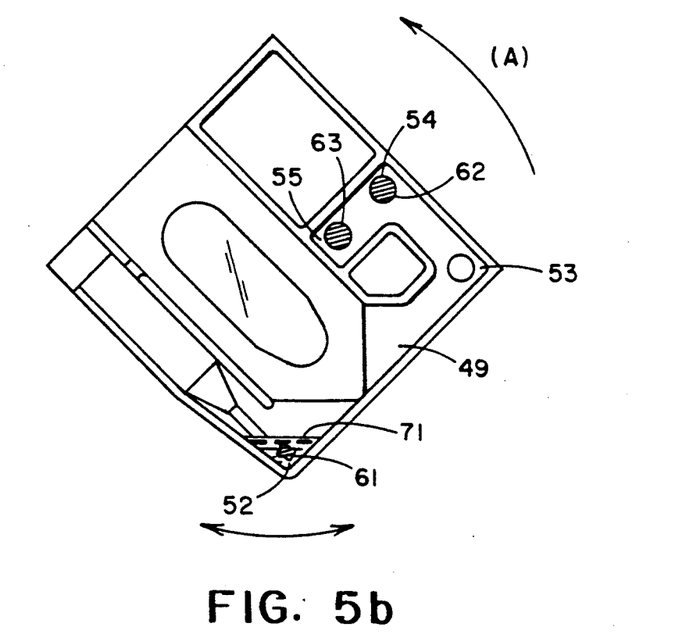
Figure 5C:
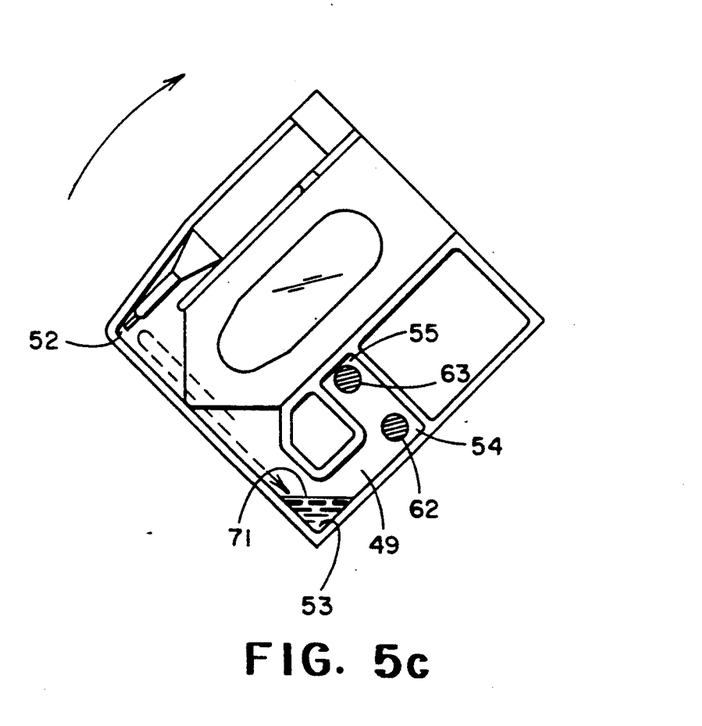
Figure 5D:
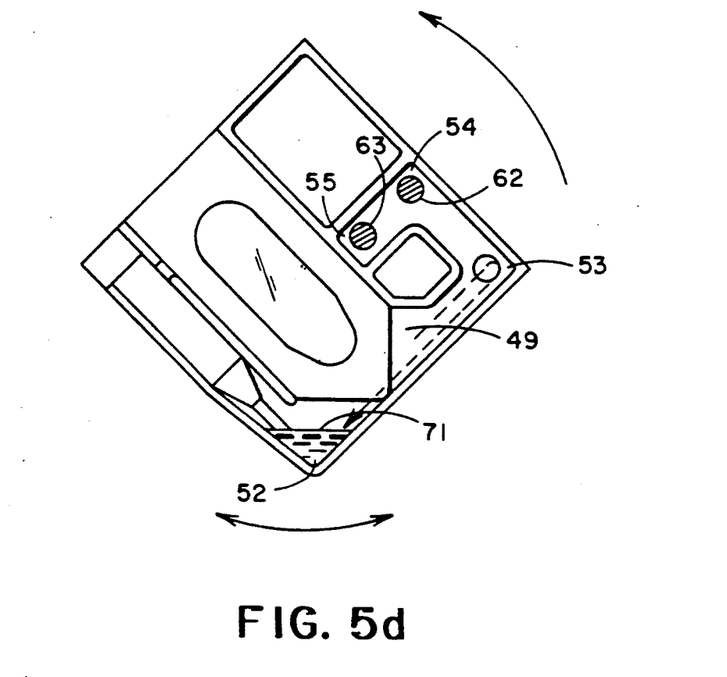

An illustrative method of using the device depicted in FIGS. 3–5 will now be described. As discussed herein, the various rotation and oscillation movements of the device can be performed manually, but in most cases will be preferably performed by a suitable instrument or apparatus. A normal first step in carrying out a test is to place a device 40 in a holder mechanism in such an instrument with device 40 positioned with corner 53 downward (FIG. 5a). Then, a liquid test sample, such as a biological fluid, is drawn into capillary tube 60 and capillary holder 41 is inserted into the positioned device 40 through opening 59 whereby capillary tube 60 becomes located in an area substantially proximate to first corner 52 and distal end 58 of capillary holder 41 closes opening 59. A lower portion 64 of side wall 44 in the area of first corner 53 is preferably configured as shown such that when capillary tube 60 is positioned as described above, capillary tube 60 is capable of being efficiently contacted by a liquid in reaction channel 49, such as a liquid reagent introduced into reaction channel 49 from liquid delivery reservoir 30.

A liquid reagent 70 contained in liquid delivery reservoir 30 is introduced into reaction channel 49 by pulling the distal end 33 of membrane 32 in a direction away from device 40 as shown by the solid arrow in FIG. 5a. Liquid reagent 70 freely flows by gravity along the path shown by the broken arrow in FIG. 5a into corner 53 of reaction channel 49. A blank absorbance measurement can be taken through cuvette window 57 at the starting position with corner 53 downward.

Figure 5E:
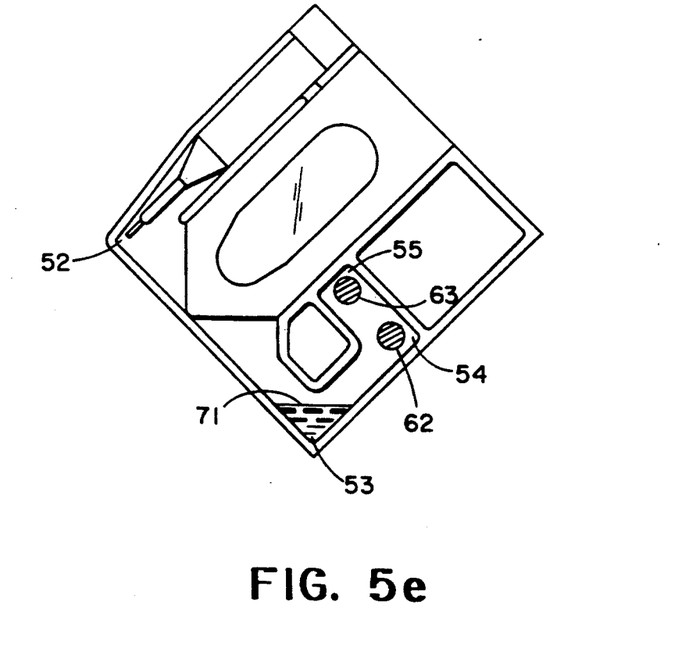

Device 40 is then rotated (FIG. 5b) in a counter-clockwise direction (arrow A) and oscillated (arrow B) whereby liquid reagent 70 is transported by gravity along reaction channel 49 and brought into contact with first corner 52, reagent zone 61, and the capillary sampling tube. It is to be understood that, according to the present invention, the turbulence caused by liquid reagent 70 impacting first corner 52 during oscillation of device 40 results in both the removal of the liquid test sample from capillary 60 and the solubilization of the first analytical reagent in reagent zone 61 to form a first reaction mixture 71 therewith as described above. If desired, device 40 can additionally be rotated in alternating clockwise and counter-clockwise directions (FIGS. 5c and 5d) wherein first reaction mixture 71 is transported by gravity along reaction channel 49 between first and second corners 52 and 53 whereby first reaction mixture 71 is further agitated and mixed in order to assure complete solubilization or suspension of the first analytical reagent. In addition, device 40 can be maintained in a stationary position for a predetermined period of time to allow the analyte in first reaction mixture 71 to sufficiently interact with the analytical reagents.

Where first reaction mixture 71 provides a first detectable response or measurable characteristic which is required or desired to be measured according to a particular assay protocol, device 40 is rotated in a clockwise direction in order that first reaction mixture 71 is transported by gravity to the cuvette window in second corner 53, and the device maintained in a stationary position (FIG. 5e). Any such first detectable response provided by first reaction mixture 71 can then be measured, and the remaining assay steps carried out subsequent thereto. For example, such first detectable response can be a total hemoglobin measurement where the liquid test sample is a whole blood sample, such as when performing an assay for the percent of glycated hemoglobin in a whole blood sample, as will be described in greater detail hereinafter.

Once the first detectable response is detected and measured in second corner 53, device 40 is rotated in a clockwise direction to transport first reaction mixture 71 by gravity from second corner 53 to reagent zone 62 in third corner 54 and in contact with the analytical reagent incorporated into reagent zone 62 to form a second reaction mixture 72 therewith (FIG. 5f) and, if desired, device 40 maintained in a stationary position to incubate second reaction mixture 72 as described above. Preferably, device 40 is oscillated in order to assure complete solubilization or suspension of the analytical reagent in reagent zone 62 and, if desired, can be additionally rotated in alternating directions to transport second reaction mixture 72 by gravity along reaction channel 49 between and in contact with corners 52, 53 and 54 in order to further mix and agitate second reaction mixture 72. It is to be understood, of course, that where a first detectable response is not provided or is not necessary or desirable to measure as described above, first reaction mixture 71 can instead be directly transported by gravity along reaction channel 49 to third corner 54 by rotating device 40 in a counter-clockwise direction.

Similarly, second reaction mixture 72 is brought into contact with fourth corner 55 and reagent zone 63 by further rotating device 40 in a clockwise direction and device 40 oscillated as described above to form a third reaction mixture 73 with the analytical reagent incorporated into reagent zone 63 and, if desired, device 40 maintained in a stationary position to incubate third reaction mixture 73 as described above. Typically, the final reaction mixture in an analytical assay procedure, in this case third reaction mixture 73, will provide a detectable response which is measured and correlated to the amount of analyte in the liquid test sample, or, where a first detectable response is provided as described above, measured and compared to the first detectable response as a function of the analyte. In either case, third reaction mixture 73 is transported by gravity along reaction channel 49 to second corner 53 by rotating device 40 in a counter-clockwise direction (FIG. 5h), and the detectable response provided thereby measured.

Device 40 can be used to perform turbidimetric and nephelometric assays in general which are known in the art to determine analytes of interest in a variety of test samples, particularly biological fluids such as whole blood, serum, plasma, urine, saliva, cerebrospinal fluid, and the like. For example, agglutination immunoassays and agglutination inhibition immunoassays can be performed wherein the analytical reagents thereof are incorporated into reaction channel 49 in the desired order sequence to be contacted by a liquid test sample and liquid reaction mixtures thereof.

In particular, device 40 according to the present invention is useful for performing an immunoturbidimetric assay for determining hemoglobin Alc (HbAlc), a glycated hemoglobin derivative. According to such assay, hemoglobin in a whole blood sample is converted into a denatured thiocyan-met-hemoglobin form which serves as the basis for first measuring total sample hemoglobin, and then measuring the denatured HbAlc form by immunoassay. The immunoassay is based on the specific interaction of an antibody particle reagent and an agglutinator reagent, such as described by U.S. patent application Ser. Nos. 118,469; 118,476 and 118,566, filed Nov. 9, 1987.

The antibody particle reagent comprises an antibody, or a fragment thereof, specific for the glycated N-terminal peptide sequence in the beta-subunit of the denatured hemoglobin, bound to a water suspendable particle (e.g., a polystyrene or other latex). Such latex particles which are useful will be evident to the worker familiar with the field of latex agglutination immunoassays. In general, such particles require the properties necessary to serve as a stable support for the desired antibody reagent for the assay and to undergo agglutination in the presence of an agglutinator reagent sufficient for analytical purposes. Latex particles are prepared generally by emulsion polymerization or suspension polymerization [Bangs, L. G. (1984) Uniform Latex Particles, Seragen Diagnostics Inc., Indianapolis, IN USA]. Swollen emulsion polymerization can also be used [Ugelstad, J., et al (1980) Adv. Colloid and Interface Sci. 13:101–140]. A good selection of latex particles are commercially available. Polystyrene particles are particularly useful.

The attachment of the antibody reagent to the latex particles is a matter of applying conventional techniques. In general, the attachment can be covalent or noncovalent. The antibody reagent can consist of whole antibodies, antibody fragments, polyfunctional antibody aggregates, and the like. Normally, whole antibody or IgG fragments such as Fab, Fab', or F(ab')$_2$ are employed. The antibody reagent can be derived by any available technique such as conventional antiserum and monoclonal techniques.

The agglutinator reagent comprises a plurality of epitopic binding sites for the antibody reagent and can be prepared according to techniques familiar to the field of agglutination immunoassays. This reagent will, in general terms, comprise a plurality of epitopic binding sites for the anti-analyte antibody reagent. Such sites can be provided by using the analyte itself or a suitable analog that retains sufficient capacity to be bound by the antibody for purposes of an assay. Such analog can, in the case of a protein analyte, comprise a suitable fragment, prepared synthetically or by digestion, comprising the epitope for the antibody reagent, e.g., glycated peptide residues of hemoglobin Alc.

The aforementioned reagents can be incorporated into device 40 in order that an immunoturbidimetric assay for HbAlc can be performed therein substantially as described above and as shown in FIGS. 5a-5h. In particular, reagent zone 61 can be incorporated with a dry, soluble form of an oxidant, such as potassium ferricyanide, and a liquid form of a denaturant 70, such as lithium thiocyanate, is contained in liquid delivery reservoir 30 which, together with the oxidant, converts the native hemoglobin to its thiocyan-met-hemoglobin form; reagent zone 62 can be incorporated with a dry, suspendable form of the antibody particle reagent; and reagent zone 63 can be incorporated with a dry, soluble form of the agglutinator reagent. A whole blood test sample or a pre-treated sample thereof, is introduced into capillary 60 and capillary holder 41 is inserted into device 40 through opening 59 (FIG. 5a), and membrane 32 manipulated as described above to introduce denaturant 70 into reaction channel 49.

Figure 5F:
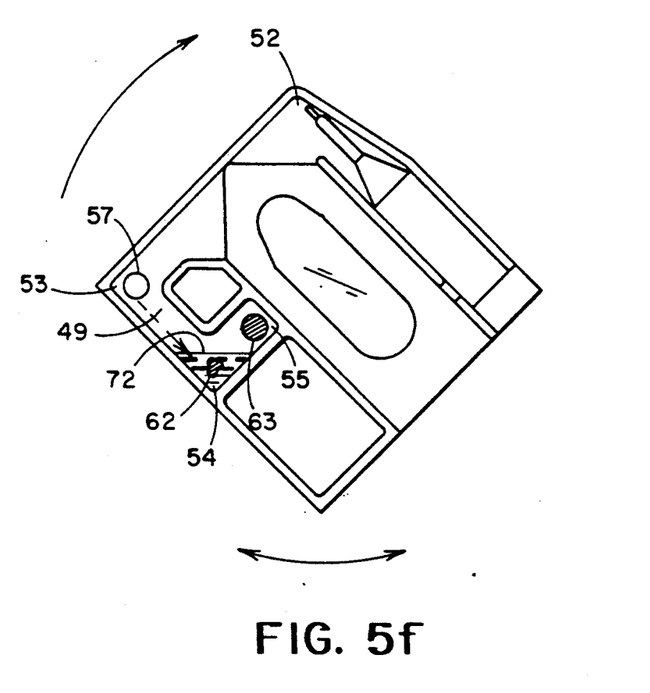
Figure 5G:
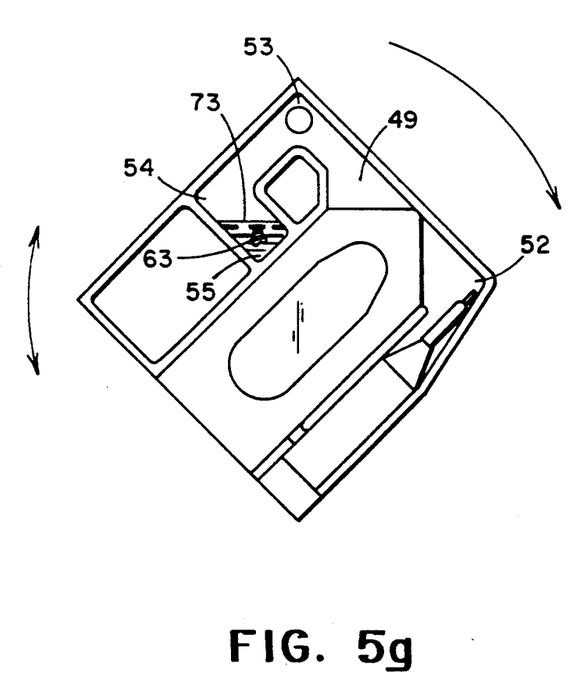

Device 40 is first rotated (FIG. 5b) in a counter-clockwise direction wherein denaturant 70 is transported by gravity along reaction channel 49 and brought into contact with first corner 52, the oxidant incorporated in reagent zone 61, and capillary 60 to form first reaction mixture 71 with the blood sample from capillary 60. Preferably, device 40 is oscillated as described above and then rotated in a clockwise direction in order that first reaction mixture is transported by gravity to second corner 53 and device 40 maintained in a stationary position (FIG. 5e). First reaction mixture 71 is preferably incubated while in second corner 53 for from between about 3-5 minutes, preferably at from between about 25° C. and about 39° C., degrees centigrade, and the total hemoglobin content determined by measuring the absorbance thereof, preferably at about 530 nm. Device 40 is then rotated in a clockwise direction to transport first reaction mixture 71 by gravity from second corner 53 to reagent zone 62 in third corner 54 and in contact with the antibody particle reagent incorporated into reagent zone 62 to form a second reaction mixture 72 therewith (FIG. 5f). Device 40 is maintained in a stationary position to incubate second reaction mixture 72 as described above, and then second reaction mixture 72 is brought into contact with reagent zone 63 at fourth corner 55 by further rotating device 40 in a clockwise direction, and device 40 oscillated as described above (FIG. 5g) to form a third reaction mixture 73 with the agglutinator reagent incorporated into reagent zone 63. It is to be understood that the antibody particle reagent and the agglutinator reagent can be situated in reaction channel 49 such that the antibody particle reagent and the agglutinator reagent are contacted either sequentially or simultaneously.

Figure 5H:
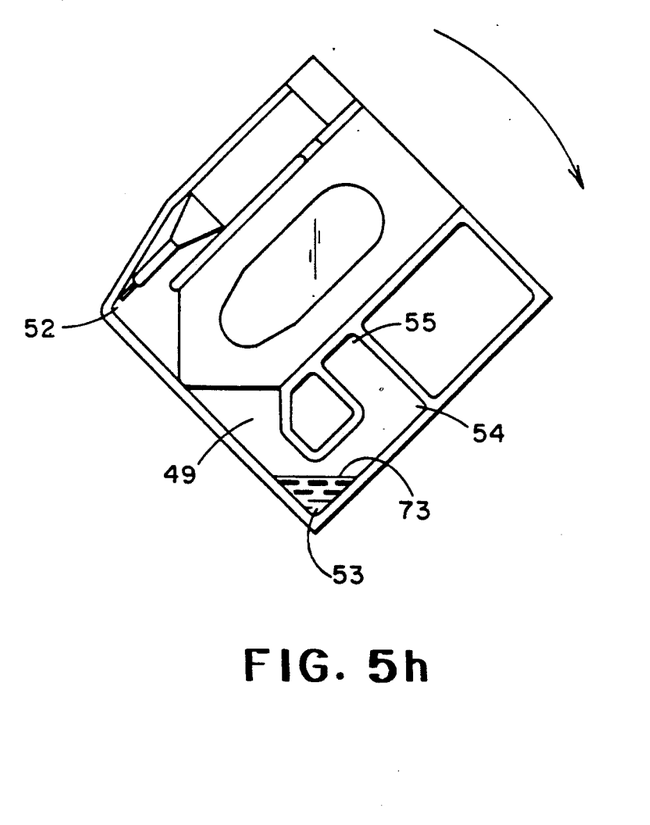

The extent to which the antibody particle and agglutinator bind to one another to form a light scattering complex is dependent on the amount of HbAlc present and is readily quantitated by turbidimetric measurement. Accordingly, the HbAlc measurement is then made by transporting third reaction mixture 73 by gravity to second corner 53 by rotating device 40 in a counter-clockwise direction (FIG. 5h). The turbidity of third reaction mixture 73 is measured as described above, and the turbidimetric response of third reaction mixture 73 and the total hemoglobin measurement of first reaction mixture 71 are correlated to the percent glycated hemoglobin in the whole blood test sample.

Device 40 is also useful for performing an immunometric assay involving binding among the analyte, a labeled reagent comprising an anti-analyte antibody reagent labeled with a detectable chemical group, and an immobilized form of the analyte or a binding analog thereof. According to such assay, the amount of labeled antibody reagent bound to the analyte from the liquid test sample or to that which is bound to the immobilized form of the analyte is determined and related to the amount of analyte present in the test sample.

The antibody component of the antibody reagent can be a whole antibody, such as any of the classes and subclasses of known immunoglobulins, e.g., IgG, IgM, and the like, or monovalent and divalent antibody fragments of IgG, conventionally known as Fab and Fab', and F(ab')$_2$ or, more preferably, a monovalent antibody fragment (Fab or Fab'). Divalent and monovalent IgG antibody fragments can be obtained according to methods known in the art employing standard proteolytic digestion procedures with pepsin or papain.

The detectable chemical group of the labeled reagent can be any material having a detectable physical or chemical property. Such materials have been well-developed in the field of immunoassays and in general any label useful in such methods can be applied to such immunometric assay procedures. For example, such chemical groups having detectable physical properties are those groups which are detected on the basis of their own physical properties which do not require a chemical reaction or interaction with another chemical or substance to provide a detectable signal, such as fluorescers, phosphorescent molecules, chromophores, radioisotopes, spin labels, or electroactive moieties. Chemical groups having detectable chemical properties are those groups which are detected on the basis of their own chemical reactivity or interaction with a detectant component therefor to provide a detectable signal. Such chemical groups having detectable chemical properties do not generate a detectable product or otherwise provide a detectable signal prior to interacting with such detectant component, and include enzymatically active groups such as enzymes, enzyme substrates, coenzymes, enzyme inhibitors and activators, chemiluminescent species, chemical catalysts, metal catalysts, members of enzyme channeling, fluorophor-quencher, or energy transfer pairs, and specifically bindable ligands such as biotin or a hapten.

The immobilized form of the analyte or binding analog thereof can be immobilized or otherwise bound to a surface of reaction channel according to methods known in the art, or incorporated as an immobilized form into a reagent pad or film as described above. Alternatively, the analyte or binding analog thereof can be immobilized to a magnetically responsive reagent particle which responds to a magnetic field without resultant permanent magnetization, commonly referred to as paramagnetic or paramagnetism. For example, such paramagnetic behavior is typically exhibited by iron oxides having a crystal size less than about 300 Å, whereas iron oxides having a crystal size greater than about 500 Å are characterized by responsiveness to a magnetic field with resultant permanent magnetization. Accordingly, such magnetically responsive reagent particles can be exposed to magnetic fields without becoming permanently magnetized, which would otherwise result in the undesirable magnetic aggregation thereof during the performance of an immunoassay.

Such magnetically responsive particles are known in the art and are commercially available, or can be prepared according to methods known in the art, such as described by U.S. Pat. No. 4,335,094 which employs a polymer having lattices or pores with a magnetic material deposited therein; U.S. Pat. Nos. 4,339,337 and 4,358,388 which employ a magnetic core surrounded by a vinylaromatic polymer; U.S. Pat. No. 4,452,773 which employs a colloidal magnetic iron oxide coated with a polysaccharide having pendant functional groups for covalently binding biological molecules thereto; and U.S. Pat. Nos, 4,554,088 and 4,628,037 which employ a metal oxide core generally surrounded by a silane coating.

Preferably, such uniform latex particles are dispersable or suspendable in aqueous media without significant gravitational settling and are therefore capable of remaining in suspension in the reaction mixture without constant mixing, i.e., water suspensible. Accordingly, together with Brownian motion and the high surface to volume ratio, efficient and rapid binding kinetics are assured.

The analyte or binding analog thereof can be immobilized to such paramagnetic particles according to methods known in the art. For example, where it is desirable to covalently bind the analyte or binding analog thereof to the magnetically responsive reagent particle, the particle should be polyfunctional or capable of being polyfunctionalized with functional groups which, for example, can be incorporated according to covalent coupling techniques known in the art [see for example, Cuatrecasas, J. Biol. Chem. Vol. 245, p. 3059(1970)]. Functional groups include carboxylic acids, aldehydes, amines, amides, activated ethylenes such as maleimide, hydroxyls, sulfonic acids, mercaptans, and the like. For example, coupling of analytes and other biological molecules to agarose and polyacrylamides is described by W. B. Jacoby and M. Wilchek, Methods in Enzymology, Vol. 34, Academic Press, New York (1974).

As will be understood by one skilled in the art apprised of the foregoing considerations, an immunometric assay employing the device can be performed by incorporating such immunometric assay reagents along reaction channel 49 as described above. It is to be understood that where the device 40 is employed to perform such immunometric assay, a buffer reagent, diluent, or the like can be contained by liquid delivery reservoir 30 and introduced into reaction channel 49 at the appropriate time. Alternatively, where the detectable chemical group of the labeled reagent possesses a detectable chemical property, such as an enzyme label, liquid delivery reservoir 30 can be incorporated with a liquid reagent containing a detectant component for such chemical group, such as a chromogenic substrate for the enzyme, and introduced into reaction channel 49 at the end of the assay to interact with the enzyme component of the labeled reagent to provide the detectable response.

The present cassette device comprises flow disrupting means to enable the critical mixing of the various reagents and materials that might be contained in a liquid mixture created within the reaction channel of the cassette. As presented in the above examples of the device, such flow disrupting means can be a wall portion of the reaction channel which forms a corner or point of convergence in the reaction channel wall. Such a corner will generally form an angle of between about 75 degrees and about 105 degrees, with an angle of about 90 degrees having been found to be particularly useful.

It will be recognized that in addition to corners, the flow disrupting means can in general comprise any structure positioned in the reaction channel which will redirect the flow of a liquid along the channel sufficient to provide the desired mixing result. For example, an alternative form of flow disrupting means could be almost any obstruction positioned in the reaction channel to deflect, redirect, or otherwise appropriately alter the flow of a liquid upon encountering the obstruction. Such an obstruction can be a solid baffle or dam structure extending perpendicularly upward from the perimeter wall that forms the reaction channel and extending transversely across the entire width of the channel, the height of such a baffle normally being less than the height of the liquid mixture as it flows along the reaction channel such that the liquid would pour over the top edge of the baffle, thereby creating a turbulence or mixing action. Alternatively, rather than a solid baffle or dam, one could form a perforated structure having apertures or vertical or horizontal slots in the baffle wall which restrict the flow of liquid through the baffle to provide the necessary mixing action. Flow disrupting means can also comprise multiple structures extending upward from the perimeter walls or transversely from the side walls, or a combination of both. It will be evident that the skilled engineer and worker in the field of flow dynamics can design even other forms of obstructions and other structures which will provide the desired agitation in the reaction channel upon oscillation of the cassette device, and therefore which can serve as the flow disrupting means of the present invention.

It has been demonstrated experimentally that the use of appropriate flow disrupting means in accordance with the present invention significantly improves the extent of mixing in the liquid test mixture. In one experiment, a comparison was made among:

(a) devices prepared in accordance with FIGS. 3–5 of the present application, and therefore comprising flow disrupting means (such devices shall be referred to as "Square Cassettes"), (b) devices prepared as described by FIGS. 1–4 of the drawings and pertinent text in commonly assigned U.S. patent application Ser. No. 179,843, filed Apr. 11, 1988, the priority of which is claimed herein (such devices operate on a similar noncentrifugal mixing principle as the present device, but are generally rounded and do not provide flow disrupting means as intended herein - such devices shall be referred to as "Round Cassettes"), and (c) Cuvettes serving as controls to which a thoroughly mixed liquid reaction mixture was added and a measurement taken ("Control Cuvettes").

The assay involved was a turbidimetric immunoassay for HbA1c as described above. The degree of mixing in the various cassettes was assessed by measuring the precision of the immunoassay conducted in the cassettes. Thorough mixing eliminated the time dependence and irreproducibility factor from the immunoassay resulting in good precision of measurement. For the Round and Square Cassettes, the antibody-latex and agglutinator reagents were dispensed in liquid form into disassembled devices at appropriate zones of the respective devices and the reagents dried, e.g., for the Square Cassette, with reference to FIG. 3 hereof, antibody-latex was located in reagent zone 62 and agglutinator in zone 63. These devices were then assembled as described above.

In carrying out immunoassays in the Square and Round Cassettes, approximately 0.5 mL of denaturant solution was added to the device and mixed with a blood test sample and the immunoassay reagents in accordance with the respective operational methods for the two types of devices. For the Control Cuvettes, the denaturant solution was first added to the device and mixed with the test sample. Thereafter, the immunoassay reagents were added in the form of a thoroughly mixed liquid solution. The agglutination response in all cassettes were then determined by turbidimetric measurement. The coefficient of variation ("CV") was then calculated for each type of device from the results of multiple test runs. The results are presented in Table A below:

TABLE A

| Device Type | CV (%) |
| --- | --- |
| Control | 1.4 |
| Round Cassette | 3.8-11.9* |
| Square Cassette | 1.5 |

*Results varied widely over this range

These experimental results demonstrate that the use of flow disrupting means in accordance with the present invention provides significant improvement in mixing and thus in the precision of the assay (Square Cassette v. Round Cassette), and that the precision thereby attained is roughly identical with that attained when premixed liquid reagents are used.

The present invention can be applied to the detection or determination of analytes in a wide variety of test samples. Any form of material can serve as the test sample provided that it is in a liquid form or can be taken up into a liquid form such as by extraction, dissolution, suspension, or the like. Normally, the test sample will be liquid in nature, and will include biological liquids such as blood, serum, plasma, urine, cerebral fluid, spinal fluid, saliva, swab extracts, sputum, and so forth. Non-biological specimens can also be processed such as industrial, food, and environmental liquids. A liquid test sample can also be the result of sample pretreatment such as dilution, filtration, concentration, chemical treatment, and so forth. These are all matters within the skill in the art.

The analytical assay procedures described above can be used in the determination of a variety of analytes. The analyte usually is a peptide, polypeptide, protein, carbohydrate, glycoprotein, steroid, nucleic acid or other organic molecule for which a binding counterpart exists or which is producible in biological systems or can be synthesized. The analyte, in functional terms, is usually selected from the group comprising antigens, haptens, complementary polynucleotide sequences, hormones, vitamins, metabolites and pharmacological agents. Usually, the analyte is an immunologically-active polypeptide or protein, usually having a molecular weight of between about 1,000 and about 10,000,000, such as an antigenic polypeptide or protein, or a hapten having a molecular weight of at least about 100, and usually less than about 1,500.

Representative polypeptide analytes are angiotensin I and II, C-peptide, oxytocin, vasopressin, neurophysin, gastrin, secretin, bradykinin, and glucagon.

Representative protein analytes include the classes of protamines, mucoproteins, glycoproteins, globulins, albumins, scleroproteins, phosphoproteins, histones, lipoproteins, including, but not intended to be limited to, apolipoproteins such as apolipoprotein-AI and apolipoprotein-B100, chromoproteins, and nucleoproteins. Examples of specific proteins are prealbumin, $\alpha$-lipoproteins, human serum albumin, $\alpha$-acid glycoprotein, $\alpha_1$-antitrypsin, $\alpha_1$-glycoprotein, transcortin, thyroxine binding globulin, haptoglobin, hemoglobin, glycated peptide sequence in the beta-subunit of human hemoglobin, myoglobulin, ceruloplasmin, $\alpha_2$-macroglobulin, $\beta$-lipoprotein, erythopoietin, transferrin, hemopexin, fibrinogen, the immunolobulins such as IgG, IgM, IgA, IgD, and IgE, and their fragments, e.g., Fc and Fab' complement factors, prolactin, blood clotting factors such as fibrinogen, thrombin and so forth, insulin, melanotropin, somatotropin, thyrotropin, follicle stimulating hormone, leutinizing hormone, gonadotropin, human chorionic gonadotropin, thyroid stimulating hormone, placental lactogen, intrinsic factor, transcobalamin, serum enzymes such as alkaline phosphatase, lactic dehydrogenase, amylase, lipase, phosphatases, cholinesterase, glutamic oxaloacetic transaminase, glutamic pyruvic transaminase, and uropepsin, endorphins, enkephalins, protamine, tissue antigens, bacterial antigens, viral antigens such as hepatitis associated antigens (e.g., hepatitis-B surface antigen, hepatitis-B core antigen, and hepatitis-B e antigen, and tumor markers (e.g., carcinoembryonic antigen, alpha fetoprotein, prostatic acid phosphatase, prostatic specific antigen, neuron specific enolase, estrogen receptor, cancer antigen 125, cancer antigen 19-9, and the like).

Representative hapten analytes include the general classes of drugs, metabolites, hormones, vitamins, toxins and the like organic compounds. Haptenic hormones include thyroxine and triiodothyronine. Vitamins include vitamins A, B, e.g., thiamine, $B_{12}$, C, D, E and K, and folic acid. Drugs include antibiotics such as aminoglycosides e.g., gentamicin, tobramycin, amikacin, sisomicin, kanamycin, and netilmicin, penicillin, tetracycline, terramycine, chloromycetin, and actinomycetin; nucleosides and nucleotides such as adenosine diphosphate (ADP) adenosine triphosphate (ATP), flavin mononucleotide (FMN), nicotinamide adenine dinucleotide (NAD) and its phosphate derivative (NADP), thymidine, guanosine and adenosine; prostaglandins; steroids such as the estrogens, e.g., estriol and estradiol, sterogens, androgens, digoxin, digitoxigenin, digitoxin, digoxigenin, 12-0-acetyldigoxigenin, and adrenocortical steroids; and others such as phenobarbital, phenytoin, primidone, ethosuximide, carbamazepine, valproate, theophylline, caffeine, propranolol, procainamide, quinidine, amitryptiline, cortisol, desipramine, disopyramide, doxepin, doxorubicin, nortryptiline, methotrexate, imipramine, lidocaine, procainamide, N-acetylprocainamide, amphetamines, catecholamines, and antihistamines. Toxins include acetyl T-2 toxin, alfatoxin, cholera toxin, citrinin, cytochalasins, staphylococcal enterotoxin B, HT-2 toxin, and the like.

It is further to be understood that the device of the present invention is not intended to be limited to performing such assay procedures as specifically described above, but can also be incorporated with analytical reagents for performing a variety of other assay procedures known in the art. For example, such other assay procedures include, but are not intended to be limited to, apoenzyme reactivation immunoassay system (ARIS) as described by U.S. Pat. No. 4,238,565; substrate labeled fluorescent immunoassay (SLFIA) as described by U.S. Pat. No. 4,279,992; enzyme inhibitor-labeled immunoassay as described by U.S. Pat. No. 4,134,792; enzyme multiplied immunoassay technique (EMIT ®) as described by U.S. Pat. Nos. 3,817,837 and 4,043,872; cloned enzyme donor immunoassay (CEDIA ®) as described in U.S. Pat. No. 4,708,929; and fluorescence polarization immunoassay (TDX ®) as described by U.S. Pat. No. 4,510,251; and the like.

The device can be manually manipulated as described above and the detectable response provided by one or more of the reaction mixtures detected and measured with an optical instrument known in the art, such as by transmission absorption or scatter, and the like. It is to be understood that body member and lid member are made to be transparent, at least in the area of a selected corner which serves as a viewing zone, to provide a viewing window to permit such optical measurement of the reaction mixtures. Where the device is manually manipulated, the support wall and the lid member are preferably transparent substantially in their entirety in order to permit an operator to observe the movement and positioning of a liquid test sample disposed in the device.

Preferably, the device is manipulated with a simple mechanical, non-centrifugal, rotating device which is adapted to receive the device in a substantially vertically orientated position as shown throughout the drawings, and which noncentrifugally rotates and oscillates the device as described above. The rotating device can be operated by, for example, an electric stepping motor which, in turn, is controlled by a microprocessor programmed to rotate the device in the desired direction and in the desired order to sequence, including stationary positions for periods of incubation, and detection and measurement of one or more of a detectable response. Such mechanical device would also include an optical system for detecting and measuring the detectable response, such as a transmission absorption or scatter optical system, which is situated in the mechanical device substantially at the horizontal axis of rotation of the device, i.e., aligned with a corner of the device. Such mechanical device could also include heating elements, such as stationary heaters or a rotating contact plate type having flexpoint connections, for heating a liquid test sample or reaction mixtures when required by a particular assay protocol, and optical sensors for properly positioning the device in the mechanical device. Preferably, the various mechanical and electronic components are housed in a conveniently sized case including, for example, a slot or opening for receiving the device or, where it is desired to simultaneously perform an assay protocol on more than one liquid test samples, more than one of the device of the present invention.

The device of the present invention can be molded or otherwise made from various moldable materials known in the art which include, but are not intended to be limited to, glass, plastics such as polystyrene, acrylic, polyethylene tetraphthalate, polycarbonate, and the like. It is to be understood that although wettable or hydrophilic materials are preferred, non-wettable or hydrophobic materials can be employed which have been pretreated as described above.

It is to be understood that the configuration of the functional walls along which a liquid test sample is guided and transported is not intended to be limited as shown and can be modified provided that they nevertheless serve to support and guide a liquid test sample therealong as described above. For example, with reference to device 40 shown in FIGS. 3 and 4, side wall 44 and inner walls 45, 46 and 50 can be V-shaped, U-shaped, or otherwise configured to provide a trough-like channel or conduit for supporting and guiding a liquid test sample therealong. In addition, support wall 47 can instead be provided as a separate element as is lid member 43 wherein first and second inner walls 45 and 46 and inner wall 50 are integral with side wall 44 and closed by such separate support wall 47 and lid member 43. Such separate support wall 47 and lid member 43 can also be in the form of a thin, flexible membrane, film, or thin plastic which can be solvent welded, laser welded, sonic welded, glued, or otherwise attached to side wall 44. The device 40 can also be modified to include an additional open body member having substantially the same dimensions of body member 42 and adapted to be closed by support wall 47 of body member 42, similar to the manner by which body member 42 is closed by lid member 43, or, alternatively, closed by an additional lid member 43. Such additional body member can be adapted to include an extension of reaction channel 49 in order to accomodate additional analytical reagents by providing, for example, a port or opening in support wall 44. This will provide open liquid flow communication between the reaction channel and such extension thereof.

Further variations and modifications for particular uses will also be evident. For example, a body or mass of absorbent material can be positioned in the cassette for the purpose of absorbing the full volume of liquid mixture in the device upon completion of the assay. In this way, no free flowing liquid would remain in the device at the time of disposal thus lessening the risk of contamination or undesirable leakage or spillage from the device. The absorbent mass would be placed, for example, at one end of the reaction channel and upon completion of the assay procedure, the device would be rotated to bring the liquid mixture into contact with the absorbent. For instance, such an absorbent means could be placed within the hollow body of capillary holder 41 where an aperture has been formed in the holder to allow flow of liquid into the hollow body upon rotation of the cassette. Also, the exterior of the device can be configured with a key element that assures proper insertion and alignment in the rotating device.

It will be apparent that other modifications and variations of the invention as herein set forth are possible without departing from the spirit and scope thereof, and that, accordingly, such limitations are imposed only as indicated by the appended claims.

What is claimed is:

1. A method for performing analytical reactions to determine an analyte in a liquid test sample, said method comprising the steps of:
   (a) providing a reaction cassette having a substantially horizontal axis of rotation, said reaction cassette comprising
      (1) inlet means for introducing a liquid test sample into said reaction cassette, and
      (2) a reaction channel is open liquid communication with said inlet means and comprising
         (i) a reagent zone incorporated with an analytical reagent which interacts with said analyte to produce a detectable response as a function of the analyte, and
         (ii) means for disrupting the flow of a liquid by gravity along said reaction channel sufficient to agitate said liquid upon contact therewith;
   (b) introducing the liquid test sample into said reaction channel of said reaction cassette through said inlet means and forming a liquid reaction mixture in said reaction channel;
   (c) rotating said reaction cassette about said horizontal axis to transport said liquid mixture by gravity along said reaction channel into contact with said analytical reagent in said reagent zone and into contact with said flow disrupting means;
   (d) oscillating said reaction cassette about said horizontal axis to agitate said liquid mixture in contact with said flow disrupting means sufficiently to thoroughly mix the test sample and analytical reagent in said mixture; and
   (e) measuring said detectable response in said liquid mixture.

2. The method of claim 1 wherein said flow disrupting means is situated along said reaction channel a sufficient distance from said reagent zone that said liquid mixture can be in contact with said reagent zone without simultaneously being in contact with said flow disrupting means.

3. The method of claim 1 wherein said flow disrupting means and said reagent zone are situated sufficiently proximate to each other that said liquid mixture can be in contact with said flow disrupting means and said reagent zone simultaneously.

4. The method of claim 1 wherein said flow disrupting means comprises an obstruction or a point of convergence in said reaction channel configured such that the gravity flow of a liquid is redirected upon contact of said liquid therewith.

5. The method of claim 1 wherein said flow disrupting means is a corner in an outer perimeter wall portion of said reaction channel which forms an angle of between about 75 degrees and about 105 degrees.

6. The method of claim 5 wherein said corner in said outer perimeter wall portion of said reaction channel forms and angle of about 90 degrees.

7. The method of claim 1 wherein the speed of rotation of said reaction cassette about said horizontal axis used to transport said liquid mixture along said reaction channel and into contact with said reagent and flow disrupting means is sufficiently slow to be essentially noncentrifugal and due substantially only to gravitational force.

8. The method of claim 7 wherein said speed of rotation is between about 1 r.p.m. and about 60 r.p.m.

9. The method of claim 1 wherein the maximum speed of rotation of said reaction cassette during its oscillation to agitate the liquid mixture in contact with said flow disrupting means is between about 15 r.p.m. and about 40 r.p.m.

10. The method of claim 1 wherein said reagent zone is incorporated with a dried form of said analytical reagent.

11. The method of claim 1 wherein said reaction cassette also comprises means for introducing a liquid analytical reagent into said reaction channel.

12. The method of claim 1 wherein said reaction cassette also comprises means for introducing a liquid test sample into said reaction channel through said inlet means.

13. The method of claim 1 wherein said reaction channel further comprises a viewing zone in open liquid flow communication with said reaction zone.

14. The method of claim 13 comprising the step of rotating said reaction cassette about said horizontal axis whereby said liquid mixture is transported by gravity along said reaction channel into said reaction mixture viewing zone.

15. The method of claim 13 wherein a second outer perimeter wall portion of said reaction channel is configured as a corner forming an angle of between about 75 degrees and about 105 degrees, and wherein said corner serves as said reaction mixture viewing zone.

16. The method of claim 1 wherein said reaction channel comprises a plurality of reagent zones incorporated with a plurality of analytical reagents, and wherein rotation of the reaction cassette about its horizontal axis is used to bring the liquid mixture in the reaction channel into contact with each such reagent zones by gravity flow.

17. The method of claim 16 wherein after being brought into contact with a reagent zone, the liquid mixture is agitated in contact with flow disrupting means by oscillation of the reaction cassette about its horizontal axis.

18. An immunoturbidometric method of determining the relative amount of glycated hemoglobin in a whole blood test sample, said method comprising the steps of:
   (a) providing a capillary holder that comprises a capillary sampling tube,
   (b) drawing said whole blood test sample into the capillary sampling tube in said capillary holder,
   (c) providing a reaction cassette having a substantially horizontal axis of rotation, said reaction cassette comprising
      (1) a reaction channel situated in the plane of rotation about said horizontal axis and comprising
         (i) an outer perimeter wall having first and second corners which form angles in said perimeter wall of between about 75 degrees and about 105 degrees,
         (ii) a first reagent zone proximal to said first corner and incorporated with an oxidant capable of converting hemoglobin into its methemoglobin form,
         (iii) a second reagent zone incorporated with an antibody-particle reagent, and
         (iv) a third reagent zone incorporated with an agglutinator reagent;
      (2) liquid delivery means for introducing an aqueous solution of hemoglobin denaturant into the reaction channel, and (3) an inlet port engageable with the capillary holder to position the capillary sampling tube proximate to said first corner of the reaction channel, (d) engaging said capillary holder in said inlet port of the reaction vessel, (e) activating said liquid delivery means to release the denaturant solution into the reaction channel of the reaction vessel, (f) rotating the reaction cassette about its horizontal axis to transport by gravity the denaturant solution along the reaction channel to said first corner of the reaction channel and into contact with the capillary sampling tube and said oxidant in said first reagent zone, (g) oxcillating the reaction cassette about its horizontal axis to agitate the denaturant solution in said first corner in contact with said capillary sampling tube and the oxidant-incorporated first reagent zone sufficiently to extract the blood sample from the capillary tube and to form a reaction mixture with the denaturant and oxidant, (h) measuring the absorbance of met-hemoglobin formed in the resulting liquid mixture, (i) rotating the reaction cassette about its horizontal axis to transport by gravity the liquid reaction mixture along the reaction channel into contact with said second and third reagent zones and said second corner, (j) oscillating the reaction cassette about its horizontal axis to agitate the liquid reaction mixture in said second corner in contact with the second and third reagent zones sufficiently to thoroughly mix said liquid mixture and the antibody-particle and agglutinator reagents, (k) measuring the absorbance of the resulting liquid mixture and relating the ratio of the absorbance measured in step (h) to such final absorbance measurement as a function of the relative amount of glycatedhemoglobin in the blood sample tested.

19. The method of claim 18 wherein said first or second corner in the reaction channel provides a viewing zone for measuring the absorbance of liquid mixtures in the reaction channel, and wherein the liquid mixtures are transported by gravity to such corner by rotation of the reaction vessel about its horizontal axis.

20. The method of claim 18 wherein said oxidant comprises a ferricyanide salt.

21. The method of claim 18 wherein said liquid denaturant comprises a thiocyanate salt.

22. The method of claim 18 wherein said antibody particle reagent comprises an antibody, or fragment thereof, to the glycated N-terminal peptide sequence in the beta-subunit of hemoglobin, which antibody or fragment is immobilized to a water suspendable particle.

23. The method of claim 22 wherein said water suspendable particle is a latex particle.

24. The method of claim 18 wherein said agglutinator reagent comprises a plurality of epitopic binding sites for said antibody reagent.

25. The method of claim 24 wherein said epitopic sites are glycated peptide residues corresponding to the glycated N-terminal peptide sequence of hemoglobin.

26. The method of claim 18 wherein said liquid delivery means is centrally located in said reaction cassette.

27. The method of claim 18 wherein said liquid delivery means is in the form of a syringe.

28. The method of claim 18 wherein said liquid delivery means is in the form of a reservoir body closed by a removable, fluid tight seal.

29. The method of claim 18 wherein said corners each form an angle of about 90 degrees.

30. The method of claim 18 wherein the speed of rotation of said reaction cassette about said horizontal axis used in steps (f) and (i) to transport liquid along the reaction channel is sufficiently slow to be essentially noncentrifugal and due substantially only to gravitational force.

31. The method of claim 30 wherein said speed of rotation is between about 1 r.p.m. and about 60 r.p.m.

32. The method of claim 18 wherein the maximum speed of rotation of said reaction vessel during its oscillation to agitate the reaction liquid in performing steps (g) and (j) is between about 15 r.p.m. and about 40 r.p.m.

33. An analytical reaction cassette for performing analytical reactions to determine an analyte in a liquid test sample, said reaction cassette having a substantially horizontal axis of rotation and comprising:

(1) inlet means for introducing a liquid test sample into said reaction cassette, and (2) a reaction channel in open liquid communication with said inlet means and comprising (i) a reagent zone incorporated with an analytical reagent which interacts with said analyte to produce a detectable response as a function of the analyte, and (ii) means for disrupting the flow of a liquid by gravity along said reaction channel sufficient to agitate said liquid upon contact therewith, whereby a liquid disposed in said reaction channel is transported by gravity along said reaction channel by rotating said reaction vessel about said horizontal axis and thereby brought into contact with said reagent zone and said flow disrupting means.

34. The reaction cassette of claim 33 wherein said flow disrupting means is situated along said reaction channel a sufficient distance from said reagent zone that a liquid can be in contact with said reaction zone without simultaneously being in contact with said flow disrupting means.

35. The reaction cassette of claim 33 wherein said flow disrupting means and said reagent zone are situated sufficiently proximate to each other that a liquid can be in contact with said flow disrupting means and said reagent zone simultaneously.

36. The reaction cassette of claim 33 wherein said flow disrupting means comprises an obstruction or a point of convergence in said reaction channel configured such that the gravity flow of a liquid is redirected upon contact of said liquid therewith.

37. The reaction cassette of claim 33 wherein said flow disrupting means is a corner in an outer perimeter wall portion of said reaction channel which forms an angle of between about 75 degrees and about 105 degrees.

38. The reaction cassette claim 37 wherein said corner in said outer perimeter wall portion of said reaction channel forms an angle of about 90 degrees.

39. The reaction cassette of claim 33 wherein said reagent zone is incorporated with a dried form of said analytical reagent.

40. The reaction cassette of claim 33 also comprising means for introducing a liquid analytical reagent into said reaction channel.

41. The reaction cassette of claim 33 also comprising means for introducing a liquid test sample into said reaction channel through said inlet means.

42. The reaction cassette of claim 33 wherein said reaction channel further comprises a reaction mixture viewing zone in open liquid flow communication with said reaction zone.

43. The reaction cassette of claim 42 wherein a second outer perimeter wall portion of said reaction channel is configured as a corner forming an angle of between about 75 degrees and about 105 degrees, and wherein said corner serves as said reaction mixture viewing zone.

44. The reaction cassette of claim 33 wherein said reaction channel comprises a plurality of reagent zones incorporated with a plurality of analytical reagents.

45. An immunoturbidimetric reaction cassette kit for determining the relative amount of glycated hemoglobin in a whole blood test sample, said kit comprising:
 (A) a capillary holder that comprises a capillary sampling tube, and
 (B) a reaction cassette body having a substantially horizontal axis of rotation and comprising
  (1) a reaction channel situated in the plane of rotation about said horizontal axis and comprising
   (i) an outer perimeter wall having first and second corners which form angles in said perimeter wall of between about 75 degrees and about 105 degrees,
   (ii) a first reagent zone proximal to said first corner and incorporated with an oxidant capable of converting hemoglobin into its methemoglobin form,
   (iii) a second reagent zone incorporated with an antibody-particle reagent, and
   (iv) a third reagent zone incorporated with an agglutinator reagent,
  whereby a liquid disposed in the reaction channel is transported by gravity along said reaction channel and into contact with said corners and said reagent zones by rotation of the reaction cassette about its horizontal axis,
  (2) liquid delivery means for introducing an aqueous solution of hemoglobin denaturant into the reaction channel, and
  (3) an inlet port engageable with the capillary holder to position the capillary sampling tube proximate to said first corner of the reaction channel.

46. The reaction kit of claim 45 wherein said liquid delivery means is centrally located in said reaction cassette.

47. The reaction kit of claim 45 wherein said liquid delivery means is in the form of a syringe.

48. The reaction kit of claim 45 wherein said liquid delivery means is in the form of a reservoir body closed by a removable, fluid tight seal.

49. The reaction kit of claim 45 wherein one of said corners serves as a reaction viewing zone from which a detectable response can be detected and measured.

50. The reaction kit of claim 45 wherein said oxidant, said antibody particle reagent, and said agglutinator reagent are incorporated as substantially dry, dissolvable forms thereof.

51. The reaction kit of claim 45 wherein said oxidant comprises a ferricyanide salt.

52. The reaction kit of claim 45 wherein said liquid denaturant comprises a thiocyanate salt.

53. The reaction kit of claim 45 wherein said antibody particle reagent comprises an antibody, or fragment thereof, to the glycated N-terminal peptide sequence in the beta-subunit of denatured hemoglobin, which antibody or fragment is immobilized to a suspendable particle.

54. The reaction kit of claim 53 wherein said suspendable particle is a water suspendable latex particle.

55. The reaction kit of claim 45 wherein said agglutinator reagent comprises a plurality of epitopic binding sites for said antibody reagent.

56. The reaction kit of claim 55 wherein said agglutinator reagent comprises glycated peptide residues of glycated hemoglobin.

57. The reaction kit of claim 45 wherein said corners each form an angle of 90 degrees.

* * * * *